(12) United States Patent
Roberts

(10) Patent No.: US 6,458,331 B1
(45) Date of Patent: Oct. 1, 2002

(54) COMPUTER INPUT DEVICE STERILIZATION METHOD AND APPARATUS

(76) Inventor: Jon L. Roberts, 529 Clear Springs Rd., Great Falls, VA (US) 22066

(*) Notice: Subject to any disclaimer, the term of this patent is extended or adjusted under 35 U.S.C. 154(b) by 0 days.

(21) Appl. No.: 09/480,755

(22) Filed: Jan. 12, 2000

Related U.S. Application Data

(63) Continuation-in-part of application No. 09/228,263, filed on Jan. 11, 1999, now Pat. No. 6,301,359, which is a continuation-in-part of application No. 09/014,559, filed on Jan. 28, 1998, now Pat. No. 6,039,928.

(51) Int. Cl.$^7$ ............................................. B01J 19/08
(52) U.S. Cl. .................................... 422/186.3; 422/24
(58) Field of Search ............................ 422/186.3, 24; 204/176

(56) References Cited

U.S. PATENT DOCUMENTS

| | | | |
|---|---|---|---|
| 3,954,407 A | 5/1976 | Andary et al. .................. 21/83 |
| 4,100,415 A | 7/1978 | Blaisdell et al. ............. 250/455 |
| 4,772,795 A | 9/1988 | Sakurai et al. ........... 250/455.1 |
| 4,806,770 A | 2/1989 | Hylton et al. ............. 250/455.1 |
| 4,973,847 A | 11/1990 | Lackey et al. ............ 250/455.1 |
| 5,023,460 A | 6/1991 | Foster, Jr. et al. ....... 250/455.1 |
| 5,126,572 A | 6/1992 | Chu ....................... 250/455.11 |
| 5,127,521 A | 7/1992 | Bourque .................. 206/362.1 |
| 5,487,877 A | 1/1996 | Choi ........................... 422/300 |
| 5,547,635 A | 8/1996 | Duthie, Jr. .................... 422/24 |
| 6,278,122 B1 * | 8/2001 | Gagnon ........................ 422/24 |

FOREIGN PATENT DOCUMENTS

| FR | 2631-240 A | * 11/1989 |
|---|---|---|
| JP | 07-160362 | 6/1995 |

* cited by examiner

Primary Examiner—Kishor Mayekar
(74) Attorney, Agent, or Firm—Roberts, Abokhair & Mardula, LLC

(57) ABSTRACT

A computer input device sterilization apparatus having ultraviolet sterilization in an enclosed container to kill bacteria and other disease carrying organisms. The invention comprises a horizontal or vertical container dimensioned to fit over computer input devices such as keyboards, mice, trackballs, touchpads and the like. An ultraviolet source within the container irradiates the computer input device with UV light which, in one embodiment generates ozone gas, thereby killing any microorganisms that might reside on the computer input devices. Ultraviolet radiation below 200 nm can also be used thereby creating ozone gas having germicidal characteristics. The ozone gas is circulated in and around the input device thereby providing further sterilization together with the ultraviolet radiation. A sterilization switch turns the UV source off when the container is opened. A timer/power circuit provides the times application of power to the UV lamps to provide UV illumination consistent with the substantial sterilization of the input device in question.

8 Claims, 3 Drawing Sheets

COMPUTER INPUT DEVICE STERILIZATION METHOD AND APPARATUS

This application is a Continuation in Part of application Ser. No. 09/228,263 filed Jan. 11, 1999 now U.S. Pat. No. 6,301,359, which is a continuation in part of application Ser. No. 09/014,559 filed Jan. 28, 1998 U.S. Pat. No. 6,039,928 from which priority is claimed.

FIELD OF THE INVENTION

The present invention relates generally to sterilization devices and methods. More particularly this invention relates to a device for sterilizing keyboards and input devices of all types using ultraviolet radiation and ozone in a semi-closed container.

BACKGROUND OF THE INVENTION

It has long been known that germs are spread by, among other things, hand to hand contact. Hence there's been much in the literature recently concerning the washing of hands in order to prevent the spreading of the common cold as well as other microbes. Further, it has long been known that toothbrushes can be a source of the spreading of germs as well. Recently, it has been discovered that bacteria continue to live on writing implements that used by individuals. Similarly disease causing germs can live on many surfaces and therefore can be a vector for the spread of disease.

There is much prior art for the sterilization of various objects. For example, hospitals use sterilization routinely for surgical instruments. Typically such sterilization occurs both chemically as well as through high-pressure high temperature steam sterilization. This results in generally sterile instruments for use in surgery. The difficulty, of course, is that such devices are expensive, cumbersome, and are therefore not practical for the widespread sterilization of more common devices.

The spread of germs via bathroom articles has been the subject of invention. Many inventors have dealt with the issues associated with toothbrush sterilization. For example, U.S. Pat. No. 3,954,407 to Andary et al. discloses an automatic toothbrush sterilization comprising ultraviolet lamps. Similarly U.S. Pat. No. 4,088,445 to Ellis discloses a sterilization holder and night light for toothbrushes. U.S. Pat. No. 4,88,4072 Ritter discloses a toothbrush sterilizer with automatic control. U.S. Pat. No. 4,772,795 to Sakurai et al. discloses an ultraviolet sterilizer for dental implements. U.S. Pat. No. 4,803,364 to Ritter discloses a toothbrush conditioner comprising an ultraviolet radiation source. U.S. Pat. No. 4,806,770 to Hylton et al. discloses another form of toothbrush holder having an ultraviolet lamp mounted within the housing.

U.S. Pat. No. 4,906,851 to Beasley et al. discloses yet another form of ultraviolet toothbrush sterilizer and holder. U.S. Pat. No. 4,973,847 to Lackey et al. discloses a toothbrush sanitation device having ultraviolet light source and a removable lid. U.S. Pat. No. 5,023,460 to Foster, Jr. et al. discloses a toothbrush sanitizer having a centrally mounted ultraviolet bulb with cavities for receiving toothbrushes. U.S. Pat. No. 5,126,572 to Chu discloses a toothbrush holder also having an ultraviolet source. U.S. Pat. No. 5,127,521 to Bourgue discloses a toothbrush holder also having an ultraviolet light source. U.S. Pat. No. 5,487,877 to Choi discloses a rest room organizer having a sterilization apparatus using ultraviolet light for sterilizing bathroom articles. U.S. Pat. No. 5,547,635 to Duthei, Jr. discloses a general sterilization method and apparatus wherein microorganisms are exposed to ultraviolet light. Thus it can be seen that much work has been done with respect to the sterilization of bathroom articles. However no similar technological attention has been paid to the sterilization of the now ubiquitous keyboard and other computer input devices which also have the potential of carrying disease producing microbes.

The only recent efforts in this regard have been the sale of sprays and soaps having some germicidal effect, which a user must spray on the keyboard or input device. Even then, only those surfaces that are directly contacted by the liquid will be sterilized to a questionable degree. It would therefore be desirable to have a convenient, commonly available, inexpensive, and easy to use sterilization method and apparatus for sterilizing keyboards and other input devices of all types and dimensions thereby preventing the transmission of object-borne disease spreading microorganisms.

SUMMARY OF THE INVENTION

It is therefore an object to the present invention to sterilize the commonly used keyboards attached to computers, word processors, typewriters and other instruments that uses such an input device.

It is yet another objective of the present invention to sterilize other input devices typically attached to computer or computer like device, such as a mouse, a trackball, touch pad and indeed any other device which comes in contact with a user's hand and which is therefore capable of carrying disease spreading microorganisms.

It is a further object of present invention to provide a keyboard and other input device sterilization apparatus that can be commonly available and easy to use without the use of liquid sprays.

It is a further object of the present invention to provide a sterilization apparatus using ultraviolet radiation as a means of sterilization.

It is a further object of present invention to combine ultraviolet sterilization and ozone sterilization together to more completely sterilize keyboards and other input devices.

It is a further object of the present invention to provide a sterilization device for sterilizing keyboards and other input devices safely and without exposing a user to ultraviolet sterilization radiation.

It is a further object of a present invention to provide a keyboard and other input device sterilization unit that operates on normal wall current or battery power.

These and other objects of the present invention will become apparent to those skilled in the art by review of the specification that follows.

The present invention is a convenience, compact, and easy to use keyboard and other input device sterilization unit (collectively "computer input device(s)"). The present invention comprises generally an ultraviolet light source particularly in the below 200 to 300 nm wavelength range. This range has long been known for its germicidal and sterilization effects achieved by direct radiation. It is also well known that ultraviolet radiation below 200 nm can produce small quantities of ozone from oxygen in the atmosphere. Ozone, in sufficient concentrations is known to have significant germicidal and sterilization effects. Further, ozone, as a gas, is able to reach certain places and crevices in keyboards such as beneath the keys and in crevices and out-of-sight surfaces that might exist on keyboards and other input devices where ultraviolet radiation might not reach.

The ultraviolet light source of the present invention is mounted within a housing such that the ultraviolet radiation can be directed onto the exposed surfaces that exist on keyboards and other input devices that can be covered by the housing. Thus the interior of the housing also can reflect ultraviolet radiation in directions such as to both directly and indirectly and reach all parts of the keyboard and other input devices to be sterilized.

The sterilization device of the present invention and its associated ultraviolet light source can be mounted in a number of configurations. For example where the keyboard or other input device is vertical or nearly so, as in the case of certain ATM machines and keypad access devices, the sterilization apparatus of the present invention can be disposed vertically, and hingedly attached to the system having the keyboard or keypad so that it can be closed over the keyboard or keypad when the keypad is not in use to perform the sterilization functions contemplated herein. The ultraviolet lamp can be a ring type lamp at the top of the housing, a tubular ultraviolet lamp source that can be suspended horizontally in the housing, a series of ultraviolet lamps that can be disposed around the perimeter of the housing thereby directing radiation inward to surfaces that are contained vertically or horizontally within the housing.

Alternatively the keyboard and other input device sterilization apparatus can be disposed horizontally and rest upon or be place over the keyboard or input device, which is to be sterilized in a substantially horizontal housing. In this instance, an ultraviolet light source could be disposed horizontally within the housing with ultraviolet radiation shining downward. Ultraviolet light sources are mounted in a portion of the housing which is closed over or placed over the keyboard or other input device allowing ultraviolet light to shine downward over any exposed surfaces where microbes might exist. Alternatively the ultraviolet radiation could come from both above and from the sides of the housing to maximize the exposed surfaces thereby having fewer surfaces within shadows, consequently maximizing the surfaces that are exposed to the sterilizing, germicidal ultraviolet rays.

The wavelength range of the ultraviolet radiation of the present invention is generally in the 200 nm to 300 nm region. However, UV radiation below 200 nm also causes a small amount of ozone to be generated. This ozone is released into the housing and together with the ultraviolet radiation provides a more complete sterilization of the surfaces covered by the sterilization apparatus of the present invention.

As noted above, in one embodiment, the present invention also comprises a housing, which is hingedly or removably attached to the keyboard or other input device thereby enclosing the keyboard or other input device within the sterilization housing. This housing prevents ultraviolet radiation from escaping the container thereby protecting any users or those who pass by the sterilization apparatus from the ultraviolet rays generated.

Integral to the housing, is a sterilization switch which is biased in the "off" position. When the housing is placed over the surface to be sterilized the switch is engaged and the ultraviolet radiation light source is turned on. When the cover is removed, for example when a keyboard or other input device is to be used, the ultraviolet radiation is immediately turned off as soon as the cover is removed or the lid is lifted.

A timer/power circuit for the ultraviolet light source is also part of present invention. The timing/power circuit is activated as soon as the housing of the sterilization apparatus is placed over the keyboard or other input device and the sterilization switch is engaged. The timer allows the ultraviolet light source to remain on for a predetermined amount of time. This time is consistent with substantial sterilization of the keyboard or other input device enclosed within the housing of the present invention. When the amount of time has expired, the ultraviolet light source is turned off thereby saving both power as well as prolonging the life of the ultraviolet light source(s). Further this limited time illumination minimizes any chemical breakdown of plastics that might occur due to ultraviolet radiation. In the event that the housing is lifted, as in the case when the keyboard or other input device is to be used, the timer is reset and, upon closing of the lid, the sterilization time period begins again.

As integral part of the sterilization apparatus of the present invention, an indicator light is provided whereby, when sterilization is proceeding, the indicator light is lit. When sterilization is not occurring, as in the case when the housing is lifted or the sterilization lamp has burned out, the indicator light is not lit. In this case it will be clear to the user that either maintenance on the device must occur or the lid is not properly engaged with the interlocking switch.

The present invention can operate both on normal current found in homes, businesses, and buildings of all types as well as on battery power. Where battery power is used it is anticipated that rechargeable batteries will be present in the present invention such that sterilization can continue to take place for some period of time even during power failures. Further, it is anticipated that power sources such as the battery of an automobile will be satisfactory to power the UV lamps of the present invention or those who wish to sterilize keyboards and other input devices while on the road.

BRIEF DESCRIPTION OF THE DRAWINGS

The present invention is now described by way of example with references to the accompanying drawings.

DETAILED DESCRIPTION OF THE INVENTION

Figure 1:
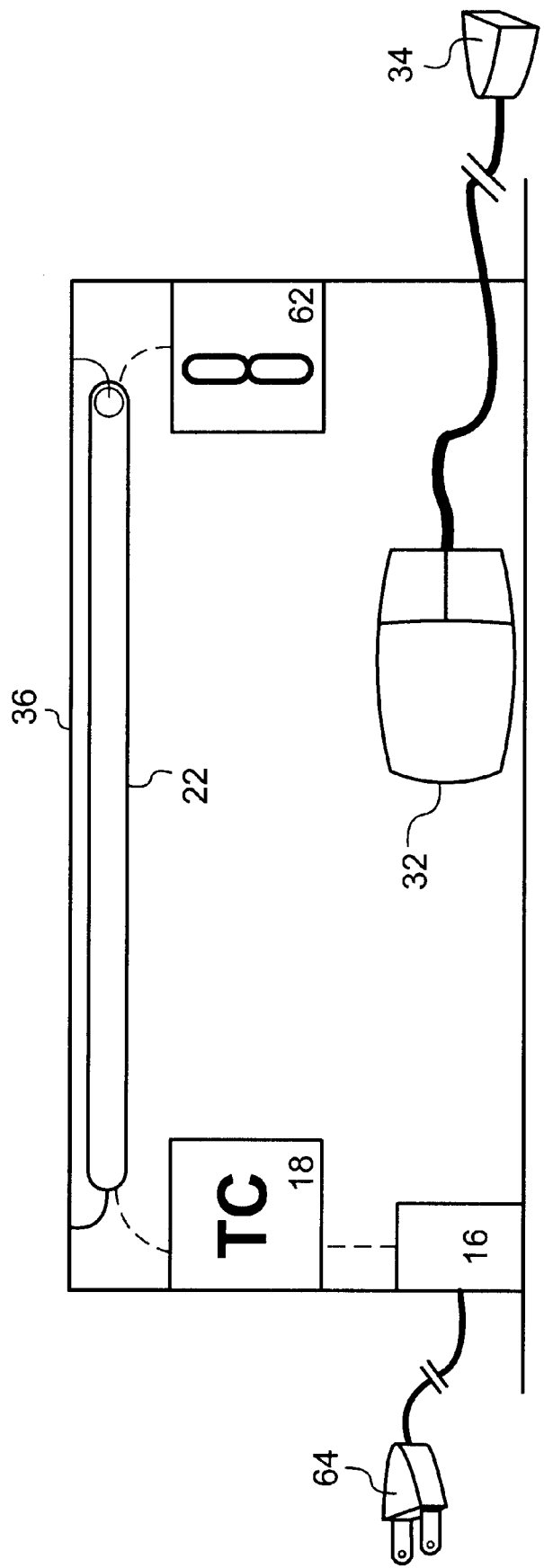
FIG. 1 illustrates a horizontally disposed version of the present invention for covering and sterilizing a keyboard.

Referring to FIG. 1 a horizontal conceptual embodiment of the present invention for covering and sterilizing a keyboard is illustrated. The sterilization apparatus of the present invention comprises the housing 10 and further comprises ultraviolet lamps 22, which are attached to the housing 10. The housing 10 is dimensioned to fit over any normal keyboard 30 of the straight or ergonomically designed type. Keyboard plug 82 plugs into the computer being used (not shown) and in this fashion, normal operations of the computer and associated keyboard are not impacted.

The number of UV lamps shown is not meant as a limitation. It will be apparent to those skilled in the art that other numbers of lamps are also appropriate depending upon the size of the lamps and the depth of the housing. For example in certain embodiments of the present invention it may be more appropriate to have more than two lamps in the housing 10 Further while the lamps are shown as individual tube type lamps, alternative shapes are well within the state-of-the-art including U-shaped lamps, ring-shaped lamps individual bulb-type lamps, and indeed any other lamp that will emit the appropriate ultraviolet radiation necessary for the sterilization.

The sterilization apparatus receives power from the typical wall outlet via a plug 64, which is connected, to an interlocking sterilization switch 16. This switch is biased in the "off" position so that when housing 10 in the open position (i.e. not place over the keyboard, all lamps, 22 are off. Conversely, when the housing is placed over the keyboard or other input device, switch 16 is closed and power is provided to lamps 22. Further when all lamps are lit indicator light (not shown) is also lit showing anyone viewing the apparatus that ultraviolet radiation is being generated by the lamps contained in the apparatus. It should be noted that the position of indicator lights is entirely arbitrary and can be placed anywhere on the apparatus to provide satisfactory convenient viewing by the user.

A protective cover for the UV lamps is also provided (but not shown in the figure) which simply protects the UV lamps from damage or contact but allows the UV illumination to shine through the protective cover and illuminate the keyboard or other input device.

As noted earlier, ultraviolet radiation in the 200 nm range generates ozone gas. In sufficient quantities ozone gas can have a germicidal effect. Therefore apertures in any protective cover for the UV tubes are provided to allow circulation of the ozone gas so that additional germicidal effects in addition to those of the ultraviolet radiation may occur. To further enhance circulation of air within the apparatus a small circulation fan 62 is provided. This fan is actuated when the sterilization switch 16 is actuated thereby providing power to the apparatus.

As part of the preferred embodiment, a timer/power circuit 18 is also provided. This timer circuit activates the ultraviolet sterilization lamps 22 as well as the recirculating fan 62 for a specific period of time. This period of time can be preset based upon the optimum time necessary to achieve sterilization. In the event that the housing 10 is not opened within the time period established in the timer circuit 18 the sterilization lamps will go off after the passage of the optimum sterilization time. In event that the housing id 10 is lifted before the time for sterilization has expired, the timer 18 is reset and, when the housing 10 is closed again, the sterilization period begins again. In this fashion power to sterilization lamps 22 is turned off after the appropriate sterilization period thereby saving lamp life and prolonging useful life of the ultraviolet sterilization lamps.

Figure 2:
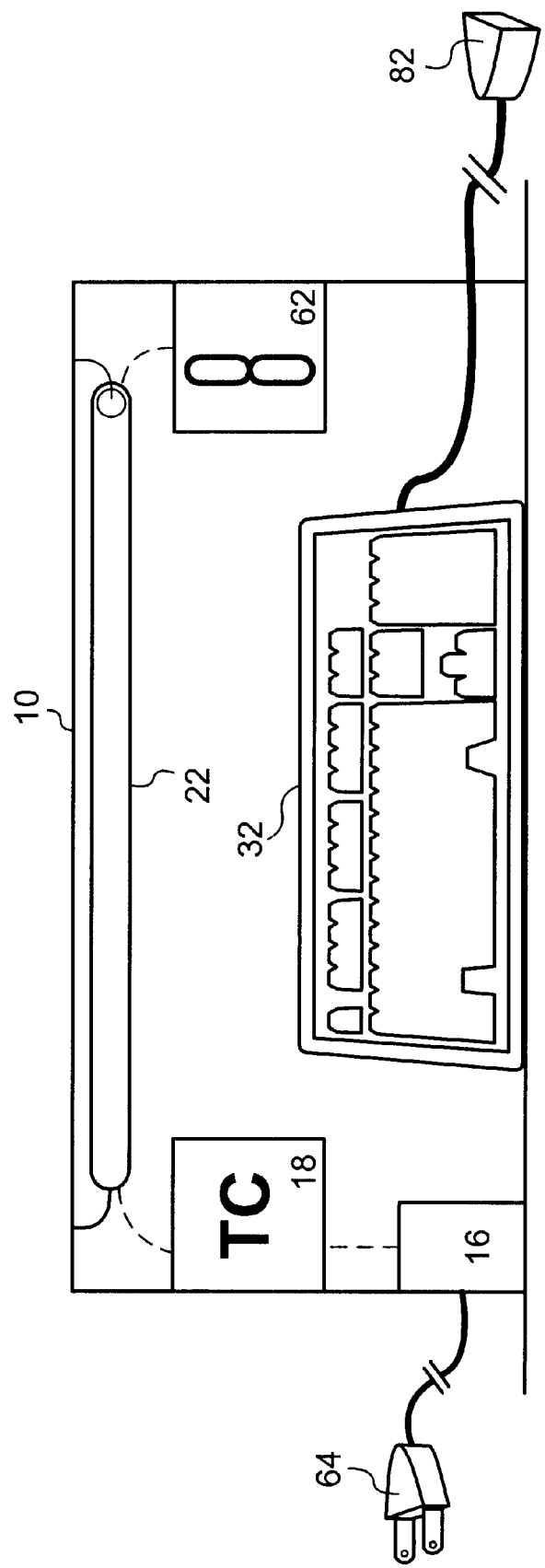
FIG. 2 illustrates a mouse or trackball version of the present invention.

Referring to FIG. 2 a mouse or trackball sterilization version of the present invention is illustrated. The sterilization apparatus of the present invention comprises the housing 36 and further comprises ultraviolet lamps 22, which are attached to the housing 10. The housing 36 in this instance is dimensioned to fit over any mouse or trackball type device 32. Mouse plug 34 plugs into the computer being used (not shown) and in this fashion, normal operations of the computer and associated input device 32 is not impacted.

Again the number of UV lamps shown is not meant as a limitation. It will be apparent to those skilled in the art that other numbers of lamps are also appropriate depending upon the size of the lamps and the depth of the housing. For example in certain embodiments of the present invention it may be more appropriate to have more than two lamps in the housing 36. Further while the lamps are shown as individual tube type lamps, alternative shapes are well within the state-of-the-art including U-shaped lamps, ring-shaped lamps individual bulb-type lamps, and indeed any other lamp that will emit the appropriate ultraviolet radiation necessary for the sterilization.

The sterilization apparatus receives power from the typical wall outlet via a plug 64, which is connected, to a sterilization switch 16. This switch is biased in the "off" position so that when housing 36 in the open position (i.e. not place over the mouse or other input device), all lamps, 22 are off. Conversely, when the housing is placed over the input device 32, switch 16 is closed and power is provided to lamps 22. Further when all lamps are lit indicator light (not shown) is also lit showing anyone viewing the apparatus that ultraviolet radiation is being generated by the lamps contained in the apparatus. It should be noted that the position of indicator lights is entirely arbitrary and can be placed anywhere on the apparatus to provide satisfactory convenient viewing by the user.

A protective cover for the UV lamps is also provided (but not shown in the figure) which simply protects the UV lamps from damage or contact but allows the UV illumination to shine through the protective cover and illuminate the keyboard or other input device.

As noted earlier, ultraviolet radiation in the 200 nm range generates ozone gas. In sufficient quantities ozone gas can have a germicidal effect. Therefore apertures in any protective cover for the UV tubes are provided to allow circulation of the ozone gas so that additional germicidal effects in addition to those of the ultraviolet radiation may occur. To further enhance circulation of air within the apparatus a small circulation fan 62 is provided. This fan is actuated when the sterilization switch 16 is actuated thereby providing power to the apparatus.

As part of the preferred embodiment, a timer/power circuit 18 is also provided. This timer circuit activates the ultraviolet sterilization lamps 22 as well as the recirculating fan 62 for a specific period of time. This period of time can be preset based upon the optimum time necessary to achieve sterilization. In the event that the housing 10 is not opened within the time period established in the timer circuit 18 the sterilization lamps will go off after the passage of the optimum sterilization time. In event that the housing id 10 is lifted before the time for sterilization has expired, the timer 18 is reset and, when the housing 10 is closed again, the sterilization period begins again. In this fashion power to sterilization lamps 22 is turned off after the appropriate sterilization period thereby saving lamp life and prolonging useful life of the ultraviolet sterilization lamps.

Figure 3:
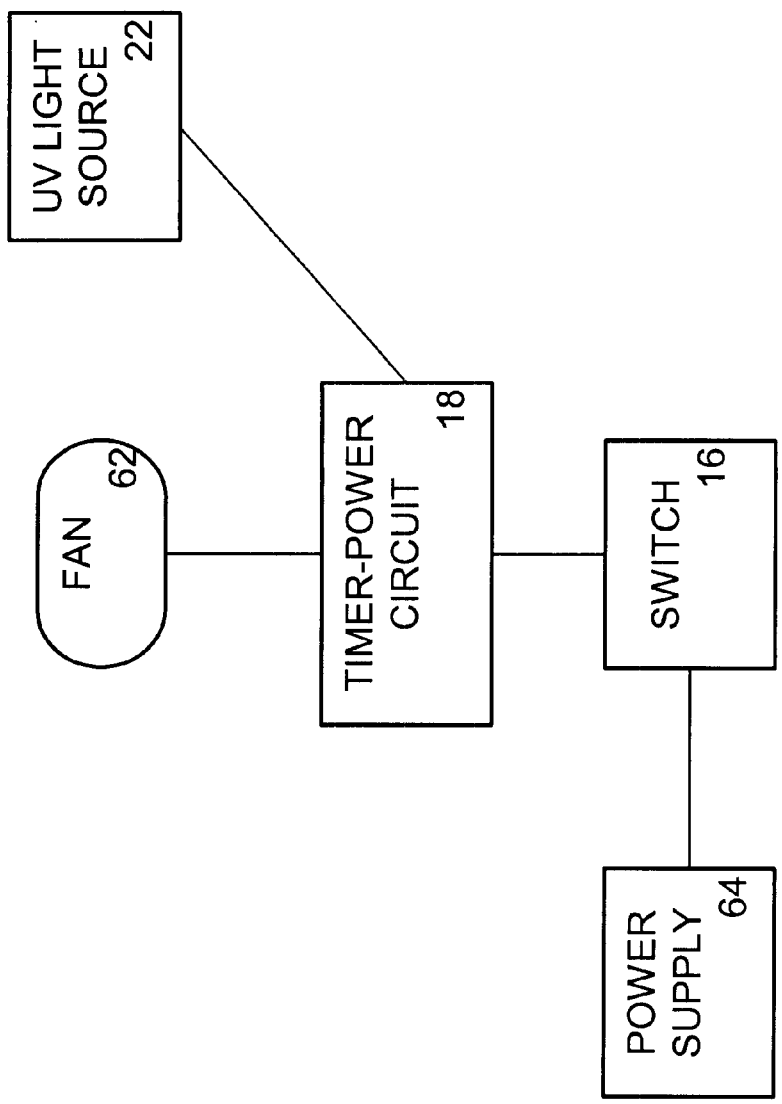
FIG. 3 is a simple schematic of the circuitry of the present invention

Referring to FIG. 3 a simplified circuit diagram of the present invention is shown. Power from conventional household power 64 is provided to the sterilization unit. Power is provided directly to the sterilization switch 16, which is normally biased to the "off" position, so that when the covers/housings of the various embodiments are closed, power is provided to the entire device.

When sterilizer switch 16 is actuated, power is provided to the timer/power switch 18 which provided a timed application of power to UV lamps 22. As noted earlier, the amount of time that power is applied to the UV lamps is consistent with substantial sterilization of the compute input device being disposed within the cover.

Whenever the sterilization lamp(s) 22 are lit an indicator lamp (not shown) is also lit thereby noting to users that ultraviolet radiation is being produced. If sterilization lamp (s) 22 is not lit either because the lamp has burned out or switch 16 is in the "off" position, the indicator light will not be lit. When the power is again provided to the sterilization lamp(s) 22, the indicator light will also be lit.

In addition, whenever power is applied to sterilization lamp(s) 22 a small circulation fan 62 is also actuated thereby circulating any ozone gas that is produced by the UV lamps of the present invention. This gas circulates in and around the keyboard or other input device that are being sterilized.

A method and apparatus for sterilization of keyboards and other input devices has been shown. Various alternative embodiments of the present invention have also been shown by reference to the figures contained herein. Common to all of these embodiments are the sterilization lamps, a cover to cover the keyboard or other input device, circulation means to circulate in any ozone produced by the ultraviolet lamps, and power and timing circuits to provide timed sterilization for writing implements that are stored in the sterilization apparatus of the present invention.

It will be appreciated by those skilled in the art that other embodiments may be possible employing the common elements of the present invention that has been disclosed.

What is claimed is:

1. A computer input device sterilizer comprising:
   a box open on one side and dimensioned to fit over and entirely cover a computer input device disposed on a surface;
   a switch biased to the off position and connected to the box so that the switch is actuated to the on position when the box is placed on the surface so as to cover the computer input device;
   a power supply connected to the switch;
   a UV light source attached to the inside of the box; and
   a timer/power circuit for providing a timed application of power from the power supply to the UV light source when the switch is actuated to the on position;
   wherein sterilization of the computer input device is effected when the box is place over the computer input device resting on the surface, causing the UV light source to emit ultraviolet radiation below 200 nm and create ozone gas.

2. The computer input device sterilizer of claim 1 wherein the UV light source emits ultraviolet radiation above 200 nm.

3. The computer input device sterilizer of claim 1 wherein the UV light source comprises a plurality of UV lamps.

4. The computer input device sterilizer of claim 1 wherein the computer input device is selected from the group consisting of: keyboards, mice, trackballs, touchpads, pen devices, and scanners.

5. A computer input device sterilizer comprising:
   a box open on one side and dimensioned to fit over and entirely cover a computer input device disposed on a surface;
   a switch biased to the off position and connected to the box so that the switch is actuated to the on position when the box is placed on the surface so as to cover the computer input device;
   a power supply connected to the switch;
   a UV light source attached to the inside of the box; and
   a timer/power circuit for providing a timed application of power from the power supply to the UV light source when the switch is actuated to the on position; and
   at least one sterilizer seal positioned to engage the surface on which the box rests for preventing UV light from the UV light source from escaping the box;
   wherein sterilization of the computer input device is effected when the box is place over the computer input device resting on the surface, causing the UV light source to emit ultraviolet radiation.

6. A computer input device sterilizer comprising:
   a box open on one side and dimensioned to fit over and entirely cover a computer input device disposed on a surface;
   a switch biased to the off position and connected to the box so that the switch is actuated to the on position when the box is placed on the surface so as to cover the computer input device;
   a power supply connected to the switch;
   a UV light source attached to the inside of the box; and
   a timer/power circuit for providing a timed application of power from the power supply to the UV light source when the switch is actuated to the on position; and
   a recirculating fan connected to the timer/power circuit for recirculating ozone gas around the computer input device within the box;
   wherein sterilization of the computer input device is effected when the box is place over the computer input device resting on the surface, causing the UV light source to emit ultraviolet radiation below 200 nm and create ozone gas.

7. A method for sterilizing a computer input device comprising:
   enclosing the computer input device in a box that is open on one side and is dimensioned to fit over the computer input device resting on a surface, the box comprising:
   a UV light source that emits UV light below 200 nm and is attached to the inside of the box;
   a timer/power circuit for providing a timed application of power connected to the UV light source;
   a sterilizer switch biased to the "off" position connected to the timer/power circuit; and
   a power supply connected to the sterilizer switch;
   generating UV light when the box is placed over the computer input device resting on the surface, thereby actuating the sterilizer switch, applying power to the timer/power circuit, thereby applying power to the UV light source, thereby producing UV light thereby killing bacteria and pathogens that may be present on the computer input device; and
   producing ozone gas thereby killing bacteria and pathogens that may be present on the computer input device.

8. The method for sterilizing a computer input device of claim 7, further comprising recirculating the ozone gas with a recirculating fan connected to the timer/power circuit.

* * * * *